(12) United States Patent
Limaye et al.

(10) Patent No.: US 10,688,256 B2
(45) Date of Patent: Jun. 23, 2020

(54) ADJUSTABLE PENETRATION DEPTH SYRINGE

(71) Applicant: Becton, Dickinson and Company, Franklin Lakes, NJ (US)

(72) Inventors: Amit Limaye, Wayne, NJ (US); Sudarsan Srinivasan, North Brunswick, NJ (US); Todd Andreoni, Lyndhurst, NJ (US); Edward J. Rosen, Morristown, NJ (US); Howard Gold, Randolph, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 8 days.

(21) Appl. No.: 15/903,474

(22) Filed: Feb. 23, 2018

(65) Prior Publication Data
US 2018/0177956 A1    Jun. 28, 2018

Related U.S. Application Data

(62) Division of application No. 14/037,904, filed on Sep. 26, 2013, now Pat. No. 9,937,299.

(51) Int. Cl.
*A61M 5/46* (2006.01)

(52) U.S. Cl.
CPC .......... *A61M 5/46* (2013.01); *A61M 2205/58* (2013.01)

(58) Field of Classification Search
CPC .............. A61M 25/0009; A61M 5/178; A61M 5/2033; A61M 2005/3118; A61M 5/34; A61M 5/343; A61M 2205/073; A61M 2205/58; A61M 5/31528; A61M 5/3153; A61M 5/31551; A61M 5/46; A61M 5/31501; A61M 5/31503; A61M 5/31505
See application file for complete search history.

(56) References Cited

U.S. PATENT DOCUMENTS

| 2,874,694 A | 2/1959 | Blackman |
| 3,895,633 A | 7/1975 | Bartner et al. |
| 4,826,490 A | 5/1989 | Byrne et al. |
| 5,010,486 A | 4/1991 | Suzuki et al. |

(Continued)

FOREIGN PATENT DOCUMENTS

| EP | 2388033 A1 | 11/2011 |
| FR | 1362060 A | 5/1964 |

(Continued)

*Primary Examiner* — Bhisma Mehta
*Assistant Examiner* — Hamza A Darb
(74) *Attorney, Agent, or Firm* — Dickinson Wright PLLC

(57) ABSTRACT

A syringe with adjustable penetration depth, comprising a tubular syringe barrel, a plunger positioned within the syringe barrel, a hub bearing a needle and attached to the syringe barrel, a movable collar having an open proximal end received over the hub, a distal end wall having an opening through which the needle protrudes, and a sidewall extending proximally from the distal end wall, the sidewall having an interior surface engaging the hub or syringe barrel, and a retaining feature on the collar engaging the hub or barrel and retaining the collar at a plurality of axial positions. The collar travels with respect to the hub along a path defined by the retaining feature on the interior surface of the sidewall engaging the hub or barrel, exposing a greater length of the needle as the collar travels toward the plunger.

16 Claims, 4 Drawing Sheets

(56) References Cited

U.S. PATENT DOCUMENTS

| | | | |
|---|---|---|---|
| 5,318,547 | A | 6/1994 | Altschuler |
| 5,466,223 | A | 11/1995 | Bressler et al. |
| 5,591,138 | A | 1/1997 | Vaillancourt |
| 6,183,440 | B1 | 2/2001 | Bell |
| 6,632,198 | B2 | 10/2003 | Caizza |
| 6,780,169 | B2 | 8/2004 | Crawford |
| 7,101,351 | B2 | 9/2006 | Crawford |
| 7,651,512 | B2 | 1/2010 | Chelak et al. |
| 8,062,252 | B2 | 11/2011 | Alheidt |
| 2001/0031949 | A1 | 10/2001 | Asbaghi |
| 2002/0004652 | A1 | 1/2002 | Asbaghi |
| 2002/0151853 | A1 | 10/2002 | Crawford |
| 2002/0193737 | A1 | 12/2002 | Popovsky |
| 2005/0187519 | A1 | 8/2005 | Harris et al. |
| 2005/0203549 | A1 | 9/2005 | Realyvasquez |
| 2008/0154192 | A1 | 6/2008 | Schraga |
| 2009/0259180 | A1* | 10/2009 | Choi ................. A61M 5/46 604/117 |
| 2010/0094216 | A1* | 4/2010 | Yue .................. A61M 5/46 604/117 |
| 2010/0274190 | A1 | 10/2010 | Wayman et al. |
| 2011/0276029 | A1 | 11/2011 | Field |
| 2012/0265156 | A1 | 10/2012 | Devereux et al. |
| 2012/0277685 | A1 | 11/2012 | Limaye |

FOREIGN PATENT DOCUMENTS

| | | |
|---|---|---|
| WO | WO-2006131832 A1 | 12/2006 |
| WO | WO-2009017277 A1 | 2/2009 |

\* cited by examiner

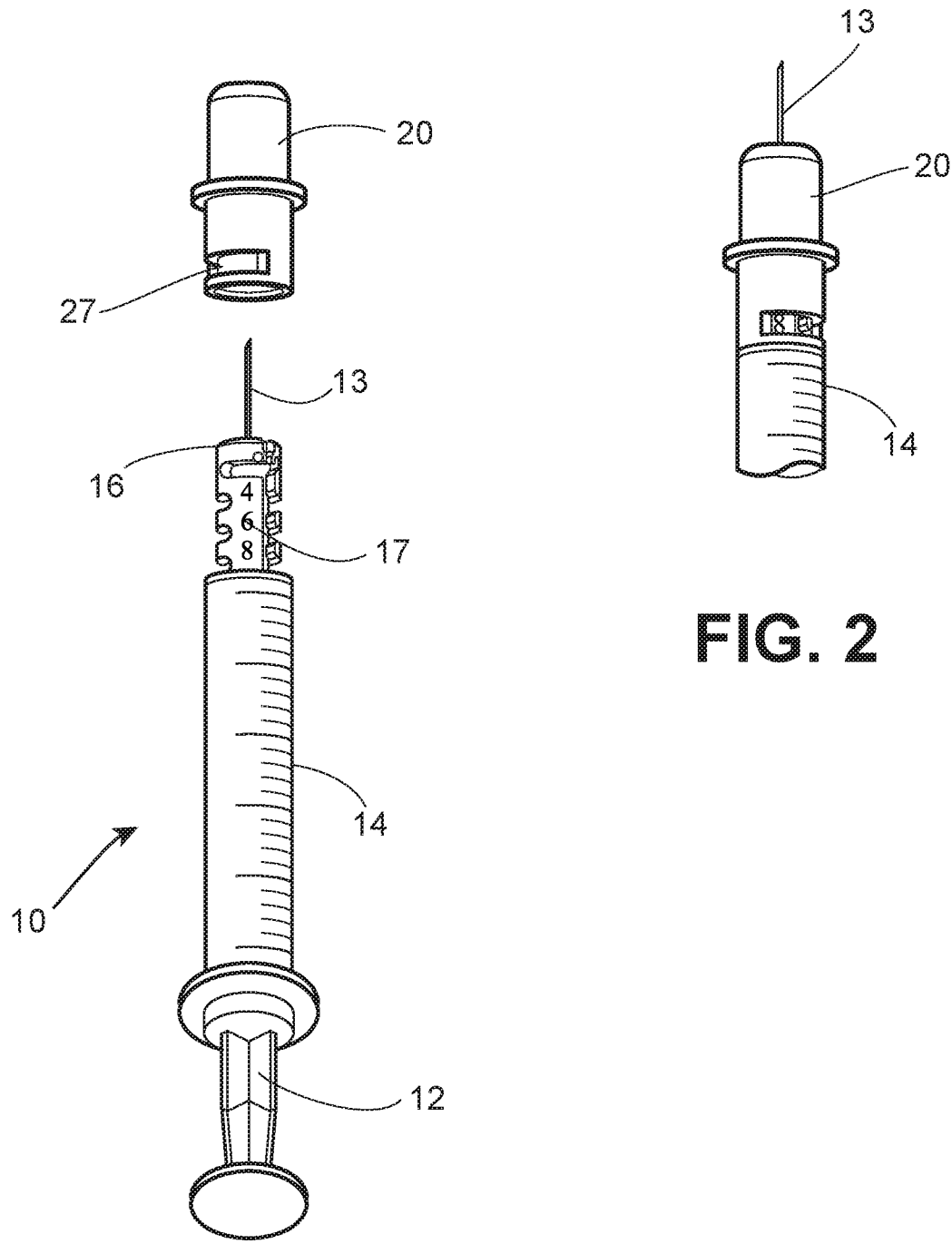

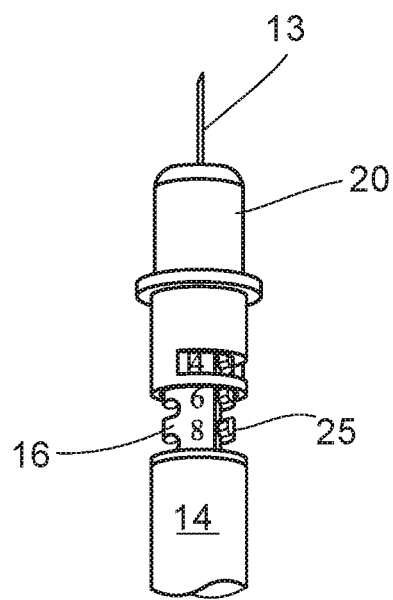
FIG. 3
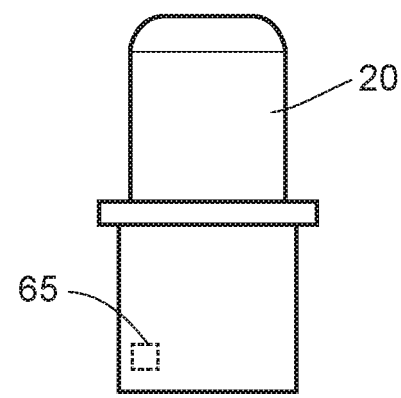
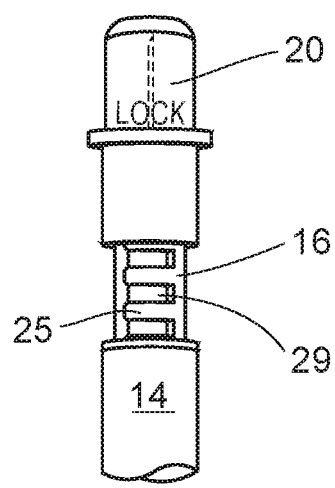
FIG. 4
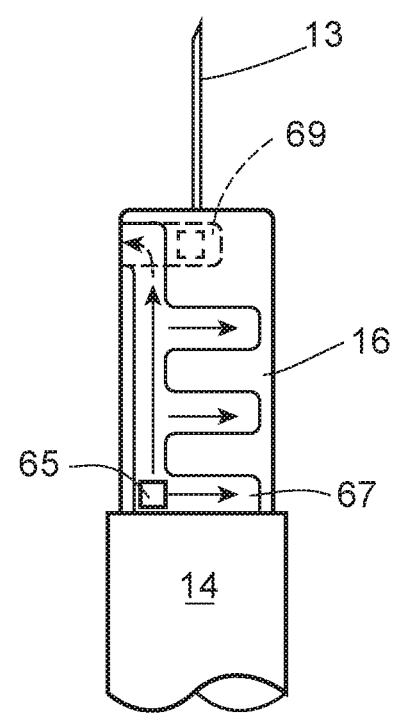
FIG. 5

ADJUSTABLE PENETRATION DEPTH SYRINGE

This application is a division of U.S. application Ser. No. 14/037,904, filed Sep. 26, 2013, issued as U.S. Pat. No. 9,937,299 B2 on Apr. 10, 2018, the entire content of said application being incorporated herein by reference.

BACKGROUND OF THE INVENTION

Field of the Invention

The invention is in the field of syringe technology. In particular, the invention is directed to a syringe having an adjustable penetration depth. The adjustable penetration depth syringe is particularly useful in the context of self-administered drugs such as insulin.

Description of the Related Art

Syringe needles preferably require a penetration depth of 6 mm to 8 mm to penetrate a vial closure. Shorter needles will not consistently penetrate the vial septum, or be able to inject air into the vial and withdraw medication. However, injection lengths shorter than 6 mm are preferred by patients and health care professionals for administering an injection. This is particularly true for injections to be delivered in the subcutaneous region, for medications such as insulin. Recent studies have also shown that the possibility of intramuscular (IM) injections increases with needle penetration depth. For administering injections in the subcutaneous region, the optimal needle length tends to be around 4 mm. Current insulin needles on the market are a fixed length, generally 6 mm, in order to properly penetrate the vial septum. These needles do not provide optimal penetration depth for injection into the subcutaneous space while minimizing risk of intramuscular injection.

U.S. Pat. No. 7,651,512 depicts a propelled lancer which optionally has an adjustable tip portion that permits a user to select a desired depth of stylet penetration from a number of depth-penetration choices. However, the lancer is not a syringe, and the design does not expose a specified needle length for an injection; in fact the needle moves within the device.

Thus, an object of the invention is to provide a syringe having an adjustable penetration depth which can be used both to fill the syringe from a vial at one penetration depth, and administer an injection at an optimal injection depth.

Another object of the invention is to provide a syringe having an adjustable penetration depth to accommodate different injection sites and different medications.

Yet another object of the invention is to provide an adjustable penetration depth device which also shields the syringe and places a protective cover over the needle cannula after use to minimize the risk of accidental needle sticks.

Yet another object of the invention combines the above advantages of adjustable penetration depth with an interchangeable needle-hub assembly, so that different gauge needles may be installed on differently sized syringes.

These and other objects of the invention are achieved with an adjustable collar received on the distal end of a syringe movable between fixed positions to adjust the penetration depth of the needle as described below.

SUMMARY OF THE INVENTION

In one aspect, the invention is a syringe with adjustable penetration depth, comprising: a tubular syringe barrel; a plunger positioned within the syringe barrel; a hub bearing a needle and attached to the syringe barrel; and a movable collar having an open proximal end received over the hub. The collar has a distal end wall having an opening through which the needle protrudes and a sidewall extending proximally from the distal end wall. The sidewall has an interior surface engaging the hub or syringe barrel and a retaining feature engaging the hub or barrel, retaining the collar at a plurality of axial positions with respect to the needle. The collar travels with respect to the hub along a path defined by features on the interior surface of the sidewall engaging the hub or barrel, exposing a greater length of the needle as the collar travels toward the plunger, and is retained in a fixed position at each of said plurality of axial positions.

In another aspect, the invention is a syringe with adjustable penetration depth, comprising a tubular syringe barrel, a plunger positioned within the syringe barrel and a hub bearing a needle attached to the syringe barrel. The hub is provided with a plurality of laterally extending protrusions defining slots at distinct axial positions on the hub. The syringe is provided with a movable collar having an open proximal end, a distal end wall having an opening through which the needle protrudes, and a sidewall extending from the distal end wall. A tab is provided on the interior surface of the sidewall adapted to be received in the slots between the laterally extending protrusions on the hub at distinct axial positions of the collar when the collar is rotated.

In another aspect, a syringe according to the invention is provided with a tubular barrel, a plunger positioned within the barrel and a hub bearing a needle attached to the barrel. A tubular adapter is attached to the distal end of the barrel. A tubular sleeve received around the adapter engages the adapter at fixed positions, exposing a longer or shorter length of needle beyond an opening in the distal end of the sleeve.

BRIEF DESCRIPTION OF THE DRAWINGS

FIG. 1 is a view of an adjustable penetration depth syringe according to an embodiment of the invention.

FIG. 2 is a detail of the distal portion of the syringe of FIG. 1 at a first penetration depth setting.

FIG. 3 is a detail of the distal portion of the syringe of FIG. 1 at a second penetration depth setting.

FIG. 4 is a detail of the distal portion of the syringe of FIG. 1 showing a collar covering and shielding the needle in a locked position.

FIG. 5 is a schematic view of a collar design showing the operation of the collar on the hub.

DETAILED DESCRIPTION OF THE INVENTION

Figure 6:
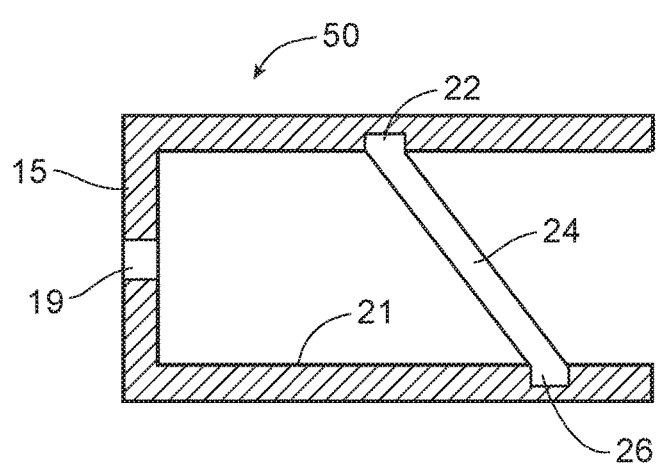
FIG. 6 is a cross sectional view of a collar design according to another embodiment of the invention.

As used herein, "axial" means along or parallel to the longitudinal axis of the needle and "radial" is the perpendicular direction. "Rotation" refers to rotation about the longitudinal axis. "Interior" means radially inward, either toward or facing the needle, and outward means radially outward or away from the needle. The "distal" direction is the direction toward the injection site and the injection end of the needle, and the "proximal" direction is the opposite direction.

As shown in the embodiment of FIG. 1, a syringe 10 according to this embodiment of the invention comprises barrel 14 having a plunger 12 therein. The plunger 12 is arranged within the syringe barrel 14 such that depressing the plunger 12 pushes a stopper through the medication compartment within the syringe barrel to pressurize the compartment and eject medication out of needle 13. A hub 16 is attached to the barrel 14, and a needle 13 is attached to the hub 16. The needle may be molded with the hub, affixed to the hub with adhesive, by welding, using a mechanical lock or other permanent means to fix the needle. The hub-needle assembly is then preferably snap-fit to the syringe barrel and is typically delivered to the user preassembled. A rotating collar 20 fits over the hub 16 and is provided with an opening on the distal end thereof through which the needle 13 protrudes. The collar 20 can be adjusted to set the penetration depth of the needle as described below.

At the setting depicted in FIG. 2, the collar is retained in its proximal-most position such that the plurality of slots is not visible, so that the open proximal end of the collar 20 abuts the syringe body 14. In this axial position, the maximum length of the needle is exposed. For example, the setting at this position may be 8 mm, and suitable for filling the syringe from a vial. Indicia 17 are provided on the hub so that the user can observe what setting is being used through a window 27 in the collar.

The bayonet-style arrangement of the collar 20 on the hub is shown in FIGS. 1-3. In this embodiment, hub 16 is snap-fit onto syringe body 14 so that the hub is preassembled as part of the syringe and not removed during ordinary use. As shown in FIG. 4, the hub is provided with lateral protrusions 25 on the hub defining slots 29 at specified increments of, for example, 1 mm each. As shown in FIG. 5, collar 20 is provided with tab 65 formed on the interior side wall of the collar 20 which can be rotated in a first direction designated by the horizontal arrows in FIG. 5 into the slots defined by lateral protrusions 25 at distinct axial positions of the collar with respect to the needle 13. Axial movement of the collar is permitted along the direction indicated by the vertical arrow in FIG. 5 when tab 65 is not engaged with any slot. For this purpose, an axially extending channel may also be provided on the radially inward surface of the collar or on the radially outward surface of the hub, engaging a corresponding member on the other of the collar or the hub, to permit smooth axial movement of the hub between different axial positions. To attain the position depicted in FIG. 3, for example, collar 20 is moved axially to a needle penetration depth of 4 mm, appropriate for an insulin injection. The user then rotates the collar 20 in the clockwise direction to set the collar at the desired penetration depth. In the embodiment shown, the window 27 in the collar sidewall permits the viewer to see the indicia on the hub which indicate the penetration depth of the needle at each setting.

As further shown in FIG. 4 and FIG. 5, at the distal most position of the collar 20, a counterclockwise turn will receive tab 65 in slot 69 attaining the "locked out" position of FIG. 4. A depression in slot 69 may receive tab 65 to inhibit clockwise rotation that would remove the collar from the locked-out state and provide a tactile indication to the user that the locked out position has been reached. Similarly, bumps or depressions may be provided in the slots at the different axial positions of the collar, providing a tactile indication for the user that the desired penetration depth of the needle has been achieved. The covering position of the collar is depicted in FIG. 4. A visual indicator may be provided to indicate the locked after-use position.

A spring (not shown) may be provided inside the collar between the distal end wall of the collar and the syringe body, biasing the collar in the distal direction, which may provide for smoother axial movement of the collar 20 on the hub 16. An internally facing flange or detent (not shown) on the collar may be used to prevent the collar from sliding distally off the hub and may also engage a corresponding feature on the hub to provide a locking action to prevent proximal or rotational movement of the collar after use. The hub-needle assembly may be provided as interchangeable units and pre-assembled with different syringe bodies. In this way, different gauge needles may be installed on different volume syringe bodies, reducing subcomponent inventory.

The cross sectional view of FIG. 6 depicts the interior of a collar according to another general embodiment of the invention. In this embodiment, collar 50 comprises a distal end wall 15 and a sidewall 21 extending proximally from the end wall and terminating in an opening large enough to accommodate the hub and in some embodiments also accommodates the distal portion of the syringe body. The sidewall 21 has an opening 19 through which the needle 13 protrudes. Channel 24 on an interior surface of the sidewall is pitched at an angle with respect to the distal end wall 15 forming a circumferential channel like a thread. When the user rotates collar 50 with respect to the syringe body, a protrusion on the hub travels in the channel 24 reaching detent 22. Preferably the hub comprises at least two protrusions on an interior surface thereof each engaging the channel. Thus, a second protrusion is received in detent 26, fixing the axial position of the collar and preventing wobble. Detents 22 and 26 act to limit rotational movement of the collar. A plurality of detent pairs may be provided in channel 24 to allow for different axial positions as the collar 20 is rotated to move proximally and distally. Protrusions which engage the channel 24 can reside on the hub or on the distal end of the syringe body. Alternatively, protrusions are provided on the collar 20, in which case a corresponding channel is provided on the hub or barrel.

FIG. 6 depicts a partial travel path, in which the collar moves axially in the course of being rotated. Alternatively, or in addition, one or more axial channels may be provided so that the collar is moved axially without rotating for all or part of the travel path. For example, the collar may be designed with a linear channel with detents at each end. The user may rotate the collar to disengage the detent, slide the collar distally or proximally along the hub to adjust the needle penetration depth, and rotate the collar again to engage detents. Multiple channels may be provided to reduce wobble or loose feel and prevent needle contact.

Figure 7:
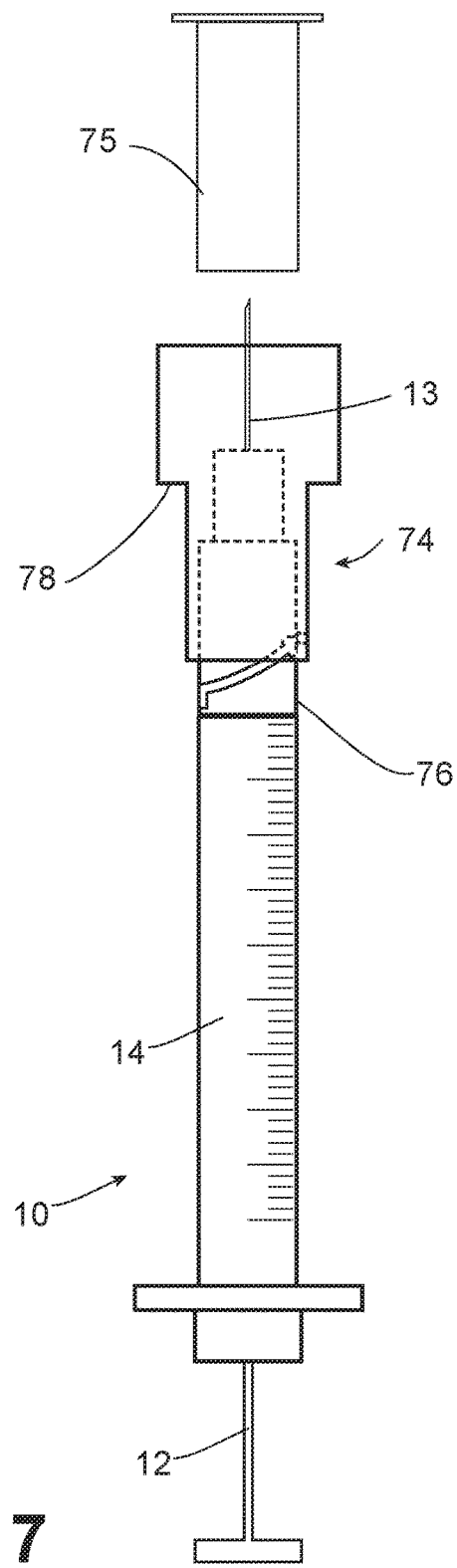
FIG. 7 is a side view of a syringe according to another embodiment of the invention having an adjustment assembly on the distal end of the syringe.
Figure 8:
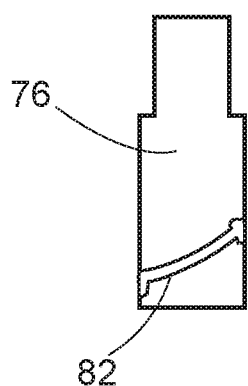
FIG. 8 depicts the adapter component of the adjustment assembly.
Figure 9:
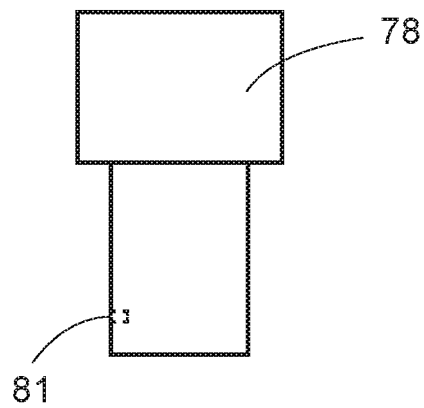
FIG. 9 depicts the sleeve component of the adjustment assembly.

Another adjustable length syringe embodiment according to the invention is depicted in FIGS. 7 through 9, wherein telescoping adjustment assembly 74 is installed on the hub at the distal end of the syringe body 14 to permit adjustment of needle penetration depth. The side view of FIG. 7 schematically depicts an integral barrel syringe, in which a needle bearing hub portion is injection molded, or otherwise formed integrally, with the syringe body. As would be apparent to one of ordinary skill in the art, the assembly 74 could also be installed on a snap fit hub, simply by varying the interface of the assembly 74 and the syringe body or hub.

In the embodiment shown, the telescoping assembly 74 comprises a tubular adapter 76 attached to the distal end of the syringe barrel using an adhesive, shrink fitting, heat staking or other means. A tubular sleeve 78 is received around the adapter 76 and is engaged with the adapter at a plurality of fixed positions, exposing a different length of needle beyond the distal end of the sleeve at each one of the plurality of fixed positions.

Figure 10:
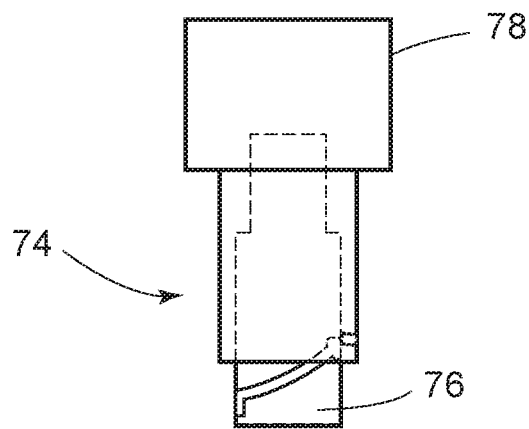
FIG. 10 depicts the assembled adjustment assembly.

As shown in FIGS. 8-10, a channel 82 is provided on the outside of the adapter 76 which engages a tab 81 on an interior surface of the sleeve 78. Alternatively, the channel may be provided on the sleeve 78 and the tab provided on the adapter. In the embodiment shown, the channel 82 has recesses at opposite ends which receive the tab 81 at different axial positions of the sleeve to retain the sleeve in position. Thus, the user can select a 4 mm, 6 mm or 8 mm penetration depth for the needle. The variations described above in connection with FIG. 6, using multiple tabs engaging detents associated with the channel, may be used to guide the sleeve travel with respect to the adapter and secure the sleeve in each of the plurality of axial positions. In addition to setting different penetration depths for the needle, the sleeve may be provided with an additional distal position, such that the distal end of the sleeve is located distally of the needle tip to minimize or prevent accidental needle stick prior to or after use. The distal end of sleeve 78 may form a skin-interfacing ring, so that the user knows that the appropriate injection depth has been reached.

In embodiments, a cap 75 is provided over the needle in the state that the device is initially encountered by the user. The cap 75 is received on the distal end of the adapter 76, between the adapter 76 and the sleeve 78, forming a sterile enclosure. Prior to administering an injection, the user manually removes any external labeling and removes cap 75 exposing the maximum penetration depth of the needle, with the sleeve in its proximal-most position. The user may choose to use this length to fill the syringe from a vial and thereafter rotate the sleeve 78 to select another depth to administer an injection. As with the foregoing embodiments, the sleeve or adapter may be provided with indicia so that the user knows what penetration depth of the needle has been selected.

In another variation, adapter 76 and sleeve 78 are provided with mating end stops. Instead of a circumferential groove in which the sleeve 78 moves axially and rotates at the same time, the sleeve is moved axially without rotation until the end stops on the adapter 76 and sleeve 78 are mated at the desired axial position of the sleeve.

The plastic parts described herein, the hub, collar(s), adapter, sleeve, etc., are typically made of injection molded polypropylene using techniques known to those having skill in the art of manufacturing syringes and medication pens. However, the invention is not limited to any particular production method. The needle is typically a standard gauge surgical stainless steel part. The adjustable length syringes may be used for any type of medication deliverable by syringe, but it is particularly preferred that the needles are used for self-injectable medications, such as insulin. The foregoing description of the preferred embodiments is not to be deemed to limit the invention, which is defined by the following claims.

What is claimed is:

1. A syringe with adjustable penetration depth, comprising:
   a tubular syringe barrel;
   a plunger positioned within the syringe barrel;
   a hub bearing a needle and attached to a distal end of the syringe barrel, the hub being removable from the syringe barrel;
   a movable collar having an open proximal end received over the hub, a distal end wall having an opening through which the needle protrudes, and a sidewall extending proximally from the distal end wall, the sidewall having an interior surface engaging the hub; and
   a retaining feature on the collar engaging the hub and retaining the collar at a plurality of axial positions; wherein
   the collar travels with respect to the hub along a path defined by the retaining feature on the interior surface of the sidewall engaging the hub, exposing a greater length of the needle as the collar travels toward the plunger;
   the collar is retained in a fixed position at a first or second axial position;
   the collar rotates without axial movement when the retaining feature on the collar is engaged to one of a plurality of slots on the hub; and
   the plurality of slots is not visible when the collar contacts the syringe barrel.

2. The syringe according to claim 1, wherein the hub bearing the needle is snap-fit to the syringe barrel and the syringe is configured to be provided pre-assembled to a user.

3. The syringe according to claim 1, further comprising indicia on the hub representing a penetration depth of the needle, said indicia being visible through an opening in the sidewall of the collar.

4. The syringe according to claim 1, wherein the hub includes a plurality of laterally extending protrusions defining the plurality of slots at distinct axial positions on the hub.

5. The syringe according to claim 4, wherein the retaining feature includes a tab adapted to engage one of the plurality of slots on the hub when the collar is rotated.

6. The syringe according to claim 5, wherein
   at least one of the plurality of slots includes a depression; and
   when the tab of the collar engages the depression, the collar is locked from further rotation.

7. The syringe according to claim 6, wherein the collar is locked at a distal most position on the collar.

8. The syringe according to claim 6, wherein when the collar is locked, a tactile indication is provided.

9. The syringe according to claim 6, wherein the collar is prevented from clockwise rotation when locked.

10. The syringe according to claim 4, wherein the plurality of slots on the hub are spaced at substantially 1 mm increments, providing for the first axial position at which 8 mm of needle length protrudes from the distal end wall of the collar, and the second axial position at which 4 mm of needle length protrudes from the distal end wall of the collar.

11. The syringe according to claim 4, wherein each of the plurality of slots is substantially perpendicular to an axis of the syringe.

12. The syringe according to claim 1, wherein
   the hub includes an axially extending channel;
   the retaining feature includes a tab; and
   the axially extending channel engages the retaining feature of the collar to allow axial movement.

13. The syringe according to claim 12, wherein the axially extending channel is substantially parallel to an axis of the syringe.

14. The syringe according to claim 12, wherein the collar travels axially without rotating when the tab on the collar is engaged to the axially extending channel on the hub.

15. The syringe according to claim 1, further comprising a visual indicator to indicate a locked after-use position.

16. The syringe according to claim 1, further comprising an internally facing flange or detent on the collar that engages the hub to provide a locking action to prevent proximal or rotational movement of the collar after use.

\* \* \* \* \*